(12) United States Patent
Hatch et al.

(10) Patent No.: US 6,210,978 B1
(45) Date of Patent: Apr. 3, 2001

(54) METHOD AND DEVICE FOR THE DETECTION OF ANALYTE IN A FLUID TEST SAMPLE

(75) Inventors: Robert P. Hatch; Meitak Teresa Yip, both of Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/032,884

(22) Filed: Mar. 2, 1998

(51) Int. Cl.7 ...................... G01N 33/548; G01N 33/553
(52) U.S. Cl. .................... 436/530; 436/525; 436/531; 436/815
(58) Field of Search .................... 436/525, 530, 436/815

(56) References Cited

U.S. PATENT DOCUMENTS 4,298,685 * 11/1981 Parikh et al. .................. 435/188

OTHER PUBLICATIONS

S. Zalipsky, Bioconjugate Chem., vol. 6, pp. 150–165. Functionalized Poly(etheylene glycol) for Preparation of Biologically Relevant Conjugates, 1995.*

* cited by examiner

*Primary Examiner*—Mary E. Ceperley
(74) *Attorney, Agent, or Firm*—Jerome L. Jeffers

(57) ABSTRACT

Disclosed is a method for the immobilization of an analyte such as deoxypyridinium (DPD) onto a solid support. The method involves binding an antigen-amino acid-deoxypyridinium complex to the support via an anti-antigen binding partner located in a capture zone of the solid support. Preferably, the support is nitrocellulose and the antigen has the fluorescein structure.

1 Claim, 1 Drawing Sheet

METHOD AND DEVICE FOR THE DETECTION OF ANALYTE IN A FLUID TEST SAMPLE

BACKGROUND OF THE INVENTION

There is a need for simple diagnostic tests for common diseases that can be executed by untrained personnel. Simpler tests would allow for home or doctor's office testing when current procedures require the analysis to be done by an outside laboratory. Possible benefits of simpler tests are decreased turnaround time and a reduction in cost. Representative examples are home pregnancy and glucose testing.

A common format for the simplified tests is the immunostrip format which comprises a solid support through which the reagents used in the test can flow by capillarity. Usually this format contains a mobile phase consisting of the test solution and an optically labeled, analyte-specific binding partner. The analyte binds to the optically labeled, analyte-specific binding partner and passes through a capture zone which contains a capture-analyte immobilized thereon. Where the capture-analyte is an analyte modified so that it can be immobilized on the capture zone of the immunostrip. The typical optical labels are gold sol or colored particles such as latex particles although other optical labels such as dye filled liposomes may be used. While optical, i.e. visually detectable, labels are preferred, this type of strip format can employ other types of detectable labels such as enzymes when the capture zone contains a substrate for the enzyme label. The capture zone captures excess labeled, analyte-specific binding partner as the labeled, analyte-specific binding partner which has combined with analyte to form an analyte/labeled specific binding partner conjugate migrates to a detection zone where the conjugate is detected.

Other formats are possible and may be advantageous. For example, it may be preferable to allow the capture-analyte to mix with the test solution before the mixture contacts the labeled, analyte-specific binding partner such that the capture-analyte and the analyte in the test solution simultaneously compete to react with the labeled, analyte-specific binding partner. The resulting mixture then migrates to the capture zone where the capture-analyte labeled analyte-specific binding partner complex and the unbound capture-analyte are captured in the capture zone. The analyte-labeled, analyte specific binding partner complex and the unbound labeled, analyte-specific binding partner continue to migrate to the detection zone where they are captured. Another example involves placing the capture-analyte in a separate zone where the capture-analyte is not immobilized so that the analyte in the test solution is allowed to first bind with the labeled analyte-specific binding partner. The mixture then migrates to the capture-analyte zone where the unbound, labeled analyte-specific binding partner is bound to the capture analyte. The final mixture migrates to the capture zone where the capture-analyte labeled, analyte-specific binding partner complex and the unbound capture-analyte are captured. The analyte-labeled, analyte-specific binding partner complex and the unbound, labeled, analyte-specific binding partner continue to migrate to the detection zone where they are captured. In a third example, the labeled, analyte-specific binding partner is mixed with the capture-analyte to form a labeled, analyte-specific binding partner complex and placed in a labeled, analyte-specific binding partner zone. When the test solution is brought into contact with the test device, the analyte in the test solution competes with the free capture-analyte to bind to the labeled, analyte-specific binding partner after which the resulting mixture migrates to the capture zone where the capture-analyte labeled, analyte-specific binding partner complex and the unbound capture-analyte are captured in the capture zone. The analyte-labeled analyte-specific binding partner complex and the unbound labeled, analyte-specific binding partner continue to migrate to the detection zone where they are captured.

In all three of the above examples, the capture-analyte is not immobilized in the test device. After the test device is contacted with the test solution, the mixture containing the labeled, analyte-specific binding partner bound to the analyte from the test solution the labeled, analyte-specific binding partner bound to the capture-analyte and the unbound capture-analyte flow to the capture zone by capillarity where the labeled, analyte-specific binding partner bound to the capture-analyte and the unbound capture-analyte compete to bind the binding reagent immobilized in the capture zone. The binding reagent is a reagent capable of binding the solid support and the capture-analyte. The labeled, analyte-specific binding partner which is not bound to the analyte moves through the capture zone, to the detection zone, and is collected by the detection reagent.

In a fourth example, the capture-analyte is immobilized by a binding reagent in the capture zone in the test device. When the test device is in contact with the test solution, the analyte in the test solution is allowed to be in contact with and bind to the labeled, ananlyte-specific binding partner first whereupon the mixture moves to the capture zone where the analyte-unbound labeled, analyte-specific binding partner is captured by the immobilized capture-analyte. The uncaptured labeled, analyte-specific binding partner then moves to the detection zone and is collected by the detection reagent. The labeled, analyte-specific binding partner binds to the capture-analyte reagent in inverse relationship to the concentration of the analyte in the test solution.

The capture-analyte and analyte binding competition for the optically labeled analyte binding partner can be variable with regard to the binding rate and the binding strength and may require variable contact times before reaching the capture zone. These formats provide alternative contact times.

There are numerous analytes whose simplified determination could be of benefit. Examples of such analytes include digoxin, thyroxine, drugs of abuse such as cocaine, and anticonvulsants such as phenobarbitol. By using the bone resorption marker deoxypyridinoline (DPD), as an illustrative example it is the intent of this invention to describe binding label-amino acid analyte reagents which act as capture-analytes to provide access to alternative formats for immobilizing an analyte onto the capture zone of an immunostrip.

SUMMARY OF THE INVENTION

The present invention involves a method for the immobilization of an analyte (or analog thereof) onto a solid support in order to form a diagnostic test device for the determination of the analyte in a fluid test sample. The solid support is contacted with a binding label-amino acid-analyte (or analyte analog) conjugate so that the binding reagent and the conjugate interact with the solid support to bind the conjugate thereto. This procedure leaves the analyte (or its analog) free to competitively bind with labeled anti-analyte when contacted with a fluid test sample in which the analyte is present.

DESCRIPTION OF THE INVENTION

Figure 1:
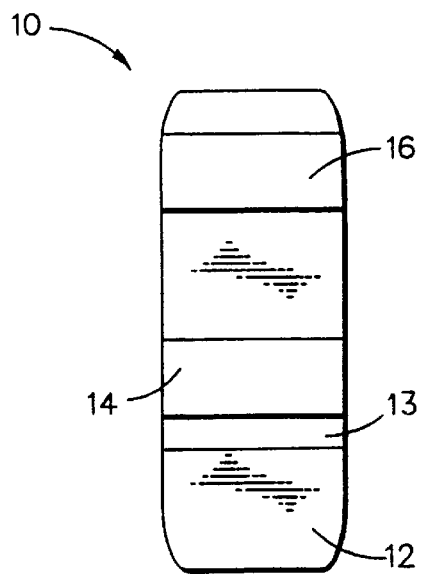
FIG. 1 represents a dry reagent test strip prepared by the method of the present invention.

A binding reagent which is capable of binding a capture-analyte through a binding label thereon is immobilized in the capture zone of an immunostrip of the type depicted in FIG. 1. The capture-analyte (in the form of a binding label-amino acid-analyte conjugate) is immobilized onto the capture zone of a solid support by the formation of a complex between a binding reagent and capture-analyte. The binding label can be an antigen or biotin. The binding reagent can be an antibody specific for the binding label antigen or avidin which binds biotin and immobilizes the capture analyte conjugate onto the solid support. For example, the binding label can be fluorescein bound to the amino group of an amino acid whose carboxyl group has been reacted with an amino group bearing analyte (or analyte analog which is specifically reactive with antibodies against the analyte) to form the binding label-amino acid-analyte conjugate. Anti-fluorescein bound to the solid support in the capture zone serves as the Binding reagent.

Collagen is present in various forms in all tissue. It is now well accepted that collagen has the form of amino acid chains cross-linked by the pyridinium crosslinks pyridinoline (PYD) and deoxypyridinoline (DPD). The pyridinium crosslinks are formed from three hydroxylysine residues, two of which are from the terminal (non-helical) peptides of the collagen molecule that are enzymatically converted to aldehydes before reaction and a third hydroxylysine situated in the helical portion of a neighboring collagen molecule. There have been described techniques in the literature for the measurement of pyridinoline in urine by use of an enzyme labeled antibody specific to pyridinoline to form a pyridinoline-enzyme labeled complex which can be detected by an enzyme-linked immunosorbant assay. While the analysis for PYD is useful as a means of screening for bone resorption and rheumatoid arthritis, its presence in connective tissue, as well as in bone, can cause skewed results. Accordingly, immunoassays for deoxypyridinoline, which is only found in bone, have become preferred over those for PYD in the early detection of bone degradation. In the following description of the present invention, DPD is illustrative of analytes whose detection may be improved by using the immobilization technique disclosed herein.

Testing for DPD can be accomplished by contacting a fluid test sample, e.g. urine, with an optically labeled antibody specific for DPD. A particularly convenient method for DPD determination involves the use of a test strip of the type depicted in FIG. 1.

Referring to FIG. 1, a test sample applied to application zone 12, of strip 10, is allowed to come into contact with an optically labeled, anti-DPD antibody (typically with gold sol as the labeling material) by capillary flow to zone 13. Any DPD in the test sample binds with the optically labeled, anti-DPD antibody to form a complex which migrates due to capillary action through the capture zone of the strip 14 and an optional detection zone 16. In the capture zone 14, there is immobilized DPD or an analog thereof which acts as a specific binding partner for the anti-DPD which captures unbound, optically labeled anti-DPD antibody. The signal generated by the label on the captured anti-DPD antibody is measured, such as by means of a reflectance spectrophotometer, and correlated with the results of replicate strips used to assay fluid test samples containing known amounts of DPD. As in classical competitive immunoassays, the intensity of the signal generated in the capture zone will be inversely proportional to the concentration of the DPD in the fluid test sample. Optically labeled anti-DPD antibody, which is not captured in the capture zone 14 because it has combined with DPD in the fluid test sample, is collected in the detection zone 16 by an antibody specific for the anti-DPD antibody such as anti-mouse IgG which is immobilized in this zone. By measuring the spectral response from the detection and capture zones, and analyzing this response using an appropriate algorithm, the accuracy of the assay can be increased.

Zone 13 contains the optically labeled anti-DPD antibody; that which hasn't reacted with DPD in the test sample, can combine with the capture DPD to become immobilized in capture zone 14. Accordingly, the key to successful operation of the type of test strip depicted in FIG. 1 is the ability to immobilize an analyte such as DPD onto the capture zone of the strip while maintaining its immunoreactivity with the labeled anti-DPD antibody.

Various formats are available for accomplishing the immobilization of DPD (or other analytes) in the capture zone. Using the fluorescein binding label example, the capture-analyte can be located in the strip's application zone 12 or a separate capture-analyte zone (not shown) so that it can mix with the labeled DPD specific binding partner thereby allowing competition for the labeled binding partner between the DPD and capture-analyte before immobilization of the capture-analyte in the capture zone 14. This embodiment may be necessary when a longer incubation time is desired. Alternatively, the labeled anti-DPD is mixed with the capture-analyte allowing complex formation in zone 13. Wetting of the strip with the test fluid will carry the complex to the capture zone while allowing competition for the labeled, anti-DPD between the analyte and free capture-analyte to take place before the capture-analyte is immobilized by interaction of the fluorescein binding label with the anti-fluorescein binding reagent to allow for binding between the capture-analyte and labeled anti-DPD, in systems where the binding reaction is weak and/or slow.

Nitrocellulose, which is commonly used to bind proteins, is a preferred material for use as the solid support in preparing the type of test strip illustrated by FIG. 1. Polysulfones and other materials which are amenable to hydrophobic interactions also provide suitable strip material. Strips for the detection/determination of DPD have been prepared by absorbing a bovine serum albumin (BSA)-DPD or polyethylene glycol (PEG)-DPD conjugate onto the nitrocellulose support; however this limits the format to one where the immobilized analyte, BSA-DPD or PEG-DPD in this case, is preimmobilized in the capture zone.

The analyte DPD is used as an example to illustrate the use of a labeled capture-analyte. The binding label-amino acid-DPD conjugate is prepared by reacting the amino acid with DPD and a binding label. As used herein the term amino acid is intended to mean a chemical entity containing one or more functional carboxylic acid groups and functional amino moieties. Particularly useful as the amino acid are polyethylene glycols which have been derivatized with carboxylic acid, e.g. carboxymethyl groups and primary amine groups at various points along the polyether chain. Any amino acid may be used with preference being given to the most common such as glycine, alanine or aminobutyric acid. Preferred binding labels are those moieties which contain the fluorescein structure, i.e.

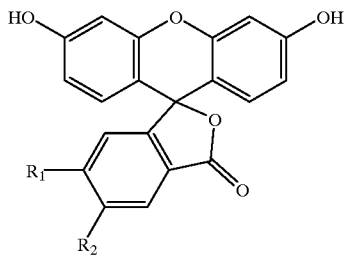

wherein $R_1$ or $R_2$ is a covalently bound amino acid linking arm and the other is hydrogen. When the amino acid is reacted with the fluorescein containing structure, the resulting fluoresceinated amino carboxylic acid provides an intermediate that can be activated by forming an ester with N-hydroxy-succinimide, or other agent such as p-nitrophenol, pentafluorephenol or pentachlorophenol, and reacting the ester with DPD. This conjugate is reacted with a binding reagent, an anti-fluorescein antibody, either before or after the antibody is bound to the solid support such as a nitrocellulose membrane to provide a substrate bearing immobilized DPD which is immunoreactive with the labeled anti-DPD antibody used in the assay. Other solid support/receptor combinations are suitable for use in the present invention. Any antibody-antigen pair can be used as long as a functionalized antigen can be prepared and covalently attached to the amino group of the amino acid. Examples include digoxin, thyroxine, and phenobarbitol. Other binding complexes such as the avidin-biotin complex can also be used.

Suitable sources of the fluorescein moiety include fluorescein isothiocyanate (FITC), fluorescein dichlorotriazinylamino, fluorescein iodoacetylfluorescein and dichlorotriazinyl fluorescein, activated esters of carboxyalkylcarbonylaminofluorescein and carboxyalkylthiocarbonylaminofluoresceins. The anti-fluorescein antibody is typically a monoclonal antibody generated against fluorescein.

The present invention is further illustrated by the following example:

EXAMPLE I

A mixture of 0.250 g (73.5 m mole) amino PEG(MW 3400) carboxylic acid from Shearwater polymers, 7.35 mg (73.5 m mole) of triethylamine as base and 31 mg (79.5 µmol) fluorescein isothiocyanate was stirred in 4 mL of dimethylformamide (DMF) under argon for 2 hours. An additional 2 µL of triethylamine was added. Ninhydrin visualization of thin-layer chromatography sample indicated that the primary amine had completely reacted with the fluorescein isothiocyanate after stirring for an additional 2 hours. The DMF was evaporated and the residue redissolved into 3 mL of methanol. The resultant was chromatographed on a 3×90 cm LH-20 column eluting with methanol. Twenty mL fractions were collected; fractions 6–10 contained the product. These were combined, evaporated, combined with 4 mL of EtOH, evaporated and then combined with 2 ml of hexane. The resulting gummy residue solidified as an orange solid to produce 0.24 g (86% theory) of the product which was dried overnight under high vacuum at 58° C.

The fluoresceinated amino PEG (MW 3400) carboxylic acid (50 mg/12.8 µmole) and 1.9 mg (16.5 µmol) of N-hydroxysuccinimide were combined. A solution of 20.6 mg/mL dicyclohexylcarbodiimide in methylene chloride was prepared and 0.16 mL (3.3 mg, 16 µmol) added to the combined solids. The mixture was allowed to stir overnight and then filtered whereupon the filtrate was concentrated and 2 mL of hexane added and evaporated to yield an orange solid.

A solution of 0.19 mL of 2.55 mg/mL DPD in 0.2 M HOAc was stirred with 0.475 mL of 0.1 M pH 8 N-(2-hydroxyethyl) piperazine-$N^1$-(3 propanesulfonic acid) (EPPS) as buffer. To this was added 5 mg of the fluoresceinated amino PEG(MW 3400) N-hydroxysuccinimide ester in 0.5 mL of DMF. The reaction was allowed to stir overnight and was then chromatographed on Pierce Kwik Sep™ polyacrylamide 1800 5 mL desalting columns. Fractions (2 mL each) were collected and monitored for free DPD using a Hewlett Packard 8452A diode array spectrophotometer at 326 nm. The background absorbance of the fluorescein group was too intense to detect DPD within the sample. The chromatography was repeated until DPD was not observed in the later fractions. Between each chromatography the product containing fractions were concentrated to a volume of 0.5 mL on a Savant Speed Vac Concentrator™ at 45° C. Two additional chromatographies were required.

EXAMPLE II

Reagents were deposited onto a nitrocellulose membrane (16 cm×6 cm) in the following manner:

Two bands of anti-mouse IgG were deposited onto the nitrocellulose membrane at about 3 and 3.5 cm from the bottom in amounts of 2 µL/cm and 1 µL/cm respectively.

Anti FITC antibody (19.2 mg/mL, 8 mL PBS) was mixed with 200 µL of FITC-PEG-DPD (0.55 mg/mL PBS) and three bands of the IgG anti FITC-FITC-PEG-DPD conjugate were deposited on the nitrocellulose membrane at about 1, 1.5 and 2 cm from the end opposite the sample application zone 12 (FIG. 1) in amounts of 2 µL/cm, 1 µL/cm and 1 µL/cm respectively. The membrane was dried, blocked with casein solution (1% in PBS), washed with water and then dried under ambient conditions.

The nitrocellulose membrane was mounted on a polystyrene backing using an acrylic based adhesive. A gold sol anti-DPD antibody pad was then assembled in zone 13 (FIG. 1) followed by the addition of an absorbant pad in zone 12 to help wick the test solution up the strip. This assembly was then slit into 4.2 (10.5 cm) inch×0.2 (0.5 cm) inch strips.

For testing, the strips were dipped into a test tube of the test solution. The test solution consisted of a stock solution having the following ingredients to which DPD was added in varying amounts.

| | |
|---|---|
| pH | 5.60 |
| calcium chloride mM | 6 |
| magnesium chloride mM | 6 |
| potassium sulfate, mM | 30 |
| urea, mM | 400 |
| ammonium sulfate, mM | 15 |
| TES buffer, mM | 24 |
| succinic acid, mM | 24 |
| sodium chloride, mM | 76 |
| 10 N NaOH, mL | 5.4 |

After the test solution had wicked to the top of the strip, the strip was removed from the test tube and scanned for response using a CLINITEK® 50 reflectance spectrometer.

Figure 2:
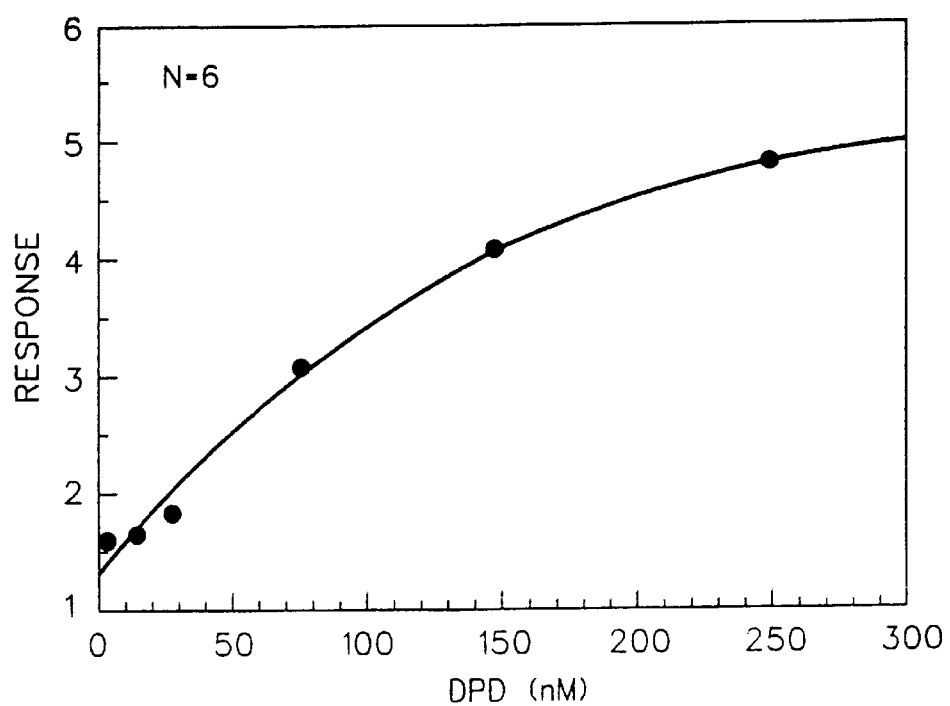
FIG. 2 is a dose response curve demonstrating the efficacy of the test strip for determining the concentration of deoxypyridinoline in a fluid test sample.

The % reflectance of the capture zone and detection zone were measured and recorded. As shown in FIG. 2, a dose/response curve was generated. This dose/response curve indicates that the DPD immobilized by the method of the present invention is immunoresponsive to this anti-DPD.

What is claimed is:

1. A method for the immobilization of deoxypyridinoline onto a solid support of nitrocellulose which method comprises contacting the solid support which has a region on its surface which bears a binding reagent of anti fluorescein antibody immobilized thereon with a solution of a conjugate of fluorescein/amino acid derivatized poly (ethylene glycol)/deoxypyridinoline so that the anti fluorescein antibody binding reagent and the fluorescein/amino acid derivatized poly (ethylene glycol)/deoxypyridinoline conjugate interact with the solid nitrocellulose support bearing the anti-fluorescein antibody by a specific reaction between the anti-fluorescein antibody binding reagent and the fluorescein/amino acid derivatized poly (ethylene glycol)/deoxypyridinoline conjugate to bind the conjugate thereto in a manner which leaves the deoxypyridinoline free to competitively bind with labeled anti-deoxypyridinoline antibody when contacted with a fluid test sample in which deoxypyridinoline is present.

* * * * *